United States Patent [19]

Reichle

[11] Patent Number: 5,354,915

[45] Date of Patent: Oct. 11, 1994

[54] CATALYSTS FOR THE REDUCTION OF CARBONYLIC COMPOUNDS TO ALCOHOLS

[75] Inventor: Walter T. Reichle, Warren, N.J.

[73] Assignee: Union Carbide Chemicals & Plastics Technology Corporation, Danbury, Conn.

[21] Appl. No.: 994,630

[22] Filed: Dec. 21, 1992

[51] Int. Cl.$^5$ .................. C07C 27/00; C07C 29/14; C07C 29/143; C07C 33/03

[52] U.S. Cl. .................. 568/881; 502/242; 568/347; 568/374; 568/391; 568/433; 568/465; 568/813; 568/820

[58] Field of Search .................. 568/881, 813, 820

[56] References Cited

U.S. PATENT DOCUMENTS

| | | | |
|---|---|---|---|
| 2,507,647 | 5/1950 | Robeson et al. | 568/881 |
| 2,767,221 | 10/1956 | Ballard et al. | 568/881 |
| 3,551,497 | 12/1970 | Wymore | 568/881 |
| 4,731,488 | 3/1988 | Shimasaki et al. | 568/814 |
| 4,847,424 | 7/1989 | Matsushita et al. | 568/484 |

OTHER PUBLICATIONS

"Acrolein" 1962 edited by Smith, p. 234.
Shibagaki et al., "Catalytic Activity of Hydrous Zirconium Oxide Calcined at Several Temperatures," *Bull. Chem. Soc. Jpn*, 63, 258–259 (1990).
Shibagaki et al., "Catalytic Reduction of Aldehydes and Ketones with 2-Propanol Over Hydrous Zirconium Oxide," *Bull. Chem. Soc. Jpn*, 61, 3283–3288 (1988).
Shibagaki et al., "Vapor–Phase Reuction of Aldehydes and Ketones with 2-Propanol Over Hydrous Zirconium Oxide," *Chemistry Letters*, pp. 1633–1636 (1988).
Kuznetsov et al., "XPS Study of the Nitrides, Oxides and Oxyntrides of Titanium," *Journal of Electron Spectroscopy and Related Phenomena*, 58(1992) 1–9.
Franklin et al., "Stabilisation and Catalytic Properties of High Surface Area Zirconia," *Catalysis Today*, 10 (1991) 405–407.
Axelsson et al., "Surface Compositional Changes of $ZrO_2$ in $H_2O$, $H_2$ and Atomic Hydrogen, Investigated by AES and EELS," *Applied Surface Science* 25 (1986) 217–230.
Morinaga et al., "Electronic Structure and Phase Stability of $ZrO_2$", *J. Phys. Chem. Solids* 44 (No. 4) 1983, pp. 301–306.
Kawai et al., "Surface Electronic Structure of Binary Metal Oxide Catalyst $ZrO_2/SiO_2$," *Surface Science III* (1981) L716–L720.
Tsuda et al., "Positron Annihilation in $ZrO_2$; Angular Correlation," *J. Phys. Soc. Jpn.* 36 (No. 2) Feb, 74 523–525.

*Primary Examiner*—Joseph E. Evans

[57] ABSTRACT

This invention provides an improved process for converting $\alpha,\beta$-olefinically unsaturated aldehydic or ketonic compounds into the corresponding allylic alcohol using an alcohol as a hydrogen donor. This process is conducted in the presence of a supported tetragonal zirconium oxide catalyst or supported $HfO_2$, $V_2O_5$, $NbO_5$, $TiO_2$ and $Ta_2O_5$ catalysts.

5 Claims, No Drawings

CATALYSTS FOR THE REDUCTION OF CARBONYLIC COMPOUNDS TO ALCOHOLS

FIELD OF THE INVENTION

The present invention relates to supported catalysts useful in organic reactions. More particularly, the present invention relates to catalysts comprising at least one metal catalyst supported on a carrier having utility in processes in which a ketone or aldehyde is converted to the respective alcohol or an alcohol is oxidized to an aldehyde or ketone.

PRIOR ART

Catalysts are generally classified according to the phase relationship between the catalyst and the reagents. A heterogeneous catalyst is in a different phase, i.e., gaseous, liquid, or solid as compared to the phase of the reagents. Heterogeneous catalysts have the advantage of being easily removed from a reaction, by techniques such as filtration. The recovery of the catalyst result in the reuse of the catalyst in the reaction and a significant cost savings. Heterogeneous catalysts can also be physically fixed in a reactor which eliminates the need to separate the catalyst from the reaction product downstream. Disadvantages of the fixed location catalysts include lower catalytic activity due to agglomeration of the catalyst or fouling of the catalyst by reaction products. In addition to the above considerations, the selection of a catalyst for a particular reaction must provide the desired product(s) at higher efficiency, while being cost effective.

Several methods are known in the prior art for converting $\alpha,\beta$-olefinically unsaturated carboxylic compounds into the corresponding $\alpha,\beta$-olefinically unsaturated alcohols, and various catalysts are disclosed for improved conversion and yields.

British Patent No. 734,247 and U.S. Pat. No. 2,763,696 disclose a process whereby acrolein may be converted to allyl alcohol by means of a vapor phase hydrogenation process. According to this process, moderate yields of allyl alcohol are obtained when acrolein is treated with free hydrogen in the vapor phase at a temperature between 210° C. and 240° C. in the presence of a catalyst comprising cadmium and one or more heavy metals of groups I, II, VI and VIII of the periodic table. Pressures on the order of 20 to 50 kilograms per square centimeter are employed in the process.

German Patent No. 858,247 discloses a somewhat different process which is also useful for the conversion of acrolein to allyl alcohol. According to the German patent, allyl alcohol is obtained by reacting acrolein with free hydrogen in the presence of a catalyst containing cadmium oxide and a metal hydrogenating component, preferably copper. The patent discloses that the best results are obtained when the process is operated at high temperatures and at high pressures on the order of 100–300 atmospheres.

It is known to convert $\alpha,\beta$-unsaturated aldehydes into the corresponding unsaturated alcohols in the liquid phase by means of hydrogenation in the presence of a mixture of a copper salt and cadmium. It is assumed by the patentees that the copper salt is the catalyst and that the cadmium salt only serves the function of preventing the copper salt from being reduced to metallic copper. The use of a solution of a mixture of a copper salt and cadmium salt for catalyst has the disadvantage that the system is extremely unstable under the required processing conditions, and fluctuations in conditions can cause reduction of the $Cd^{+2}$ salt and/or the $Cu^{+2}$ salt to metals.

U.S. Pat. No. 3,686,333 describes a liquid phase hydrogenation process for converting alkenals into alkenols in the presence of a catalyst mixture of a cadmium salt of a fatty acid and a transition metal salt of a fatty acid.

Japanese Patent No. 73-01,361 discloses a process for hydrogenating $\alpha,\beta$-olefinically unsaturated aldehydes into the corresponding allylic alcohol derivatives. The efficiency of the process is improved by the recycle of by-products to the hydrogenation zone, or by passage of the by-products stream into a second hydrogenation zone. The preferred catalysts are mixtures of cadmium and copper, cadmium and silver, cadmium and zinc, cadmium and chromium, copper and chromium, and the like. The Japanese patent discloses that under steady state conditions 1.5 moles/hour of acrolein are converted to 1.05 moles/hour of allyl alcohol and 0.4 mole/hour of n-propanol.

Shibageki et al. discloses the reduction of aldehydes with 2-propanol by catalysis with hydrous zirconium oxide (100% unsupported) to give the corresponding alcohol. See for example, Bull. Chem. Soc. Jpn., 61, 3283–3288 (1988); Bull. Chem. Soc. Jpn., 63, 258–259 (1990); and Chemistry Letters, p. 1633–1636 (1988). The hydrous zirconium oxide was prepared by reacting zirconium oxychloride ($ZrOCl_2$) with sodium hydroxide at room temperature and the resulting precipitate was washed free of resulting chloride ion yielding a hydrated zirconium hydroxide-oxide.

Despite the teachings of the prior art, a need exists for a heterogeneous catalyst for the reduction of aldehydic or ketonic compounds having high catalytic activity which can either be easily removed from the reaction products or more preferably, can be fixed in the reactor and regenerated to maintain high catalytic activity.

SUMMARY OF THE INVENTION

The present invention provides a predominately tetragonal $ZrO_2$ catalyst supported on a neutral support. As used herein, "predominately" is understood to mean greater than 50 percent. The novel catalyst can be advantageously employed in the reaction of an $\alpha,\beta$-olefinically unsaturated aldehydic or ketonic compound with an alcohol to form the corresponding allylic alcohol derivative. Since this reaction is reversible, the catalyst is also effective in the oxidation of an allylic alcohol to the corresponding unsaturated aldehydic or ketonic derivative. Other catalysts found to be effective in these reactions include supported $TiO_2$, $Nb_2O_5$, $V_2O_5$, $HfO_2$ and $Ta_2O_5$ catalysts on a neutral support.

DETAILED DESCRIPTION OF THE INVENTION

The predominately tetragonal $ZrO_2$ catalyst is prepared by impregnating a neutral support to incipient wetness. Incipient wetness as used herein is defined as the volume of solution needed to thoroughly wet the catalyst support but not leave excess liquid present. In effect this fills the catalyst support pores and coats the catalyst support external surface with the liquid.

The zirconium-containing solution and support are well mixed until the support absorbs the zirconium solution. The zirconium-containing support is air dried and then oven dried at a temperature between about 250° C. and about 350° C., preferably about 300° C. for a period of from about 2 to about 4 hours, preferably for about 3 hours. The high temperature drying for the extended period of time is necessary to volatilize or drive off anions from the surface of the support.

The supports should have no or substantially no Lewis or Brönsted acid or base sites. Submersion of the support into neutral water should not cause the pH of the water to vary by more than (±1) pH unit. Suitable supports include but are not limited to silica, various carbons, germanium oxide, and aluminas, of which silica is preferred.

The support is preferably a high surface area support, generally containing from about 10 to about 1000 square meters/gram, preferably from about 150 to about 500 and most preferably from about 200 to about 400 square meters/gram. The pore volume of the support typically ranges from 0.1 to about 2.0 cubic centimeters per gram and preferably ranges from 0.5 to about 1.5 cubic centimeters per gram.

The support can be in any desired physical shape. For example the support can be a powder, wire, chips, or a shaped piece such as wire, strip, coil or bead. In general the form or shape of the support depends on the design of the reactor employed. Determining the shape or form of the support is readily appreciated by one with ordinary skill in the art. High surface area silica beads (5-10 mesh particles or ⅛" to ¼" extrudates) are readily available from suppliers such as Philadelphia Quartz Co. or W.R. Grace & Company.

The zirconium source deposited on the silica is important in preparing the catalyst. The zirconium-containing compound is soluble in a solvent and must contain an anion which decomposes upon heating or an anion which is volatile. The zirconium-containing compound must be soluble in a solvent so that a uniform coating of the support with the zirconium-containing compound is achieved. Illustrative of the zirconium-containing compounds which may be employed include, but not limited to, aqueous $ZrO(NO_3)_2$, $ZrOCl_2$, $ZrCl_4$, $Zr(OCH(CH_3)_2)_4$ in isopropanol, $Zr(OCH(CH_3)_2)_4$ in ethanol/acetic acid solution and a $ZrO_2$ colloidal dispersion in water (approximately 0.01 micron $ZrO_2$). Especially preferred is aqueous $ZrO(NO_3)_2$.

The amount of zirconium oxide deposited on the support may vary from about 0.1 to about 25.0 weight percent, preferably from about 1.0 to about 11.0 and most preferably from about 2.0 to about 8.0 weight percent.

The supported $TiO_2$, $Nb_2O_5$, $V_2O_5$, $HfO_2$ and $Ta_2O_5$ catalysts, here after referred to as the metal oxide catalysts, are prepared in a similar manner to the supported $ZrO_2$ catalyst. The support is impregnated with the metal-containing solution, e.g. Ti, Nb, etc., to incipient wetness. The support is then allowed to absorb the solution and is dried at room temperature. The metal-impregnated support is then oven-dried at a time and temperature using a procedure similar to that used in producing the supported $ZrO_2$ catalyst. As with the supported $ZrO_2$ catalyst, the metal-containing solution must contain an anion which decomposes upon heating or an anion which is volatile in order to provide the desired metal oxide catalyst. Suitable titanium, niobium, vanadium, hafnium and tantalum-containing solutions will be readily apparent to those with ordinary skill in the art.

The amount of metal oxide catalyst deposited on the support may vary from 0.1 to about 25 weight percent, preferably from about 1.0 to about 11.0 and most preferably from about 2.0 to about 8.0 weight percent.

The tetragonal zirconium oxide and metal oxide supported catalyst are advantageously employed in an improved process for converting α,β-olefinically unsaturated aldehydic or ketonic compounds to the corresponding alcohol in the presence of a catalyst. This reaction is commonly known to those in the art as the Meerwein-Ponndorf-Verly (MPV) reduction. See Wilds, *Org. Reactions*, 2, 178 (1944). The reverse reaction is an Oppenauer oxidation with alcohols being oxidized by ketones or aldehydes in the presence of catalytic compound, typically aluminum alkoxide. See Djerassi, *Organic Reactions*, 6,207 (1951).

The MPV/Oppenauer reactions are represented by the following reversible equations.

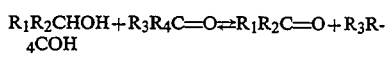

wherein $R_1$, $R_2$, $R_3$ and $R_4$ are hydrogen or hydrocarbon radicals containing between 1 and 18 carbon atoms. Suitable hydrocarbon radicals include alkyl, aryl, alkyl-substituted aryl groups and the like. $R_1$ and $R_2$ may be the same or different and $R_3$ and $R_4$ may be the same or different provided that $R_1$, $R_2$, $R_3$ and $R_4$ are not the same.

A cyclic mechanism appears to prevail in the MPV reaction in which the α-hydrogen of the alcohol is transferred with its pair of electrons to the carbonyl carbon of the ketone; this results in the ketone/aldehyde of the alcohol and an alcohol from the reagent ketone/aldehyde. This reaction can be driven to the product side by excess of alcohol and by distilling off a low boiling product, e.g., acetaldehyde or acetone. When the alcohol has an α-D, e.g., $(CH_3)_2CDOH$, then the deuterium atom transfers to the α-carbon of the reduced ketone.

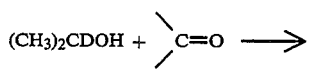

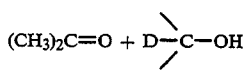

The MPV reaction is normally carried out in homogeneous solution using aluminum tri(isopropoxide) as catalyst and isopropanol as the preferred reducing agent/catalyst combination. A low boiling product, such as acetone, is distilled off as it appears in the reaction to shift the equilibrium to the product side. The inverse procedure is conducted for the Oppenauer oxidation, e.g., when an appropriate alcohol is oxidized using a ketone or aldehyde as the oxidizing agent the removal of the generated aldehyde or ketone drives the reaction to the product side.

The α,β-olefinically unsaturated carbonylic compounds used in the present process invention include those which correspond to the formula:

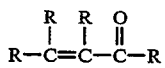

wherein R is a substituent selected from hydrogen and hydrocarbon radicals containing between one and 18 carbon atoms. The R substituents can be the same or different. More preferably R is a substituent select from the group hydrogen and alkyl groups containing 1 to 4 carbon atoms. Illustrative of $\alpha,\beta$-olefinically unsaturated compounds which can be selectively reduced or oxidized in accordance with the invention process include but are not limited to acrolein, methacrolein, crotonaldehyde, tiglic aldehyde, $\alpha$-ethylacrolein, cinnamaldehyde, hexanal, methyl vinyl ketone, methylisopropenyl ketone and alcohols such as cinnamyl alcohol, isopropanol and the like. Halogen and nitrogen substituents may also be selectively reduced to allylylic derivatives.

Alcohols are the hydrogen donors in the MPV reaction being oxidized to ketone or aldehydes. Generally a secondary alcohol such as isopropanol is preferred, however other alcohols including but not limited to 2-butanol and ethanol may also be employed.

In the practice of the process, the $\alpha,\beta$-olefinically unsaturated carbonylic compound and alcohol are passed through a reaction zone containing supported $ZrO_2$, $Ta_2O_5$, $TiO_2$, $Nb_2O_5$, $V_2O_5$ or $HfO_2$ catalysts and mixtures thereof. The reaction can be carried out in the liquid or gas phase.

The reaction temperature of the process can vary in the range between about 50° C. and 250° C. and preferably between about 150° C. and 225° C. The pressure of the hydrogenation process can vary in the range between about 15 and 1000 psia and preferably between about 200 and 550 psia, and most preferably between about 400 and 550 psia.

The mole ratio of the alcohol to $\alpha,\beta$-olefinically unsaturated aldehydic or ketonic compound in the feed can vary in the range between about 1:1 and 1000:1, preferably between about 2:1 and 25:1 and most preferably between about 5:1 and 20:1.

The rate at which the alcohol and aldehydic or ketonic compound contact the catalyst is not critical. The feed rate can be varied with other conditions to optimize aldehyde/ketone conversion and yield of the unsaturated alcohol. The liquid hourly space velocity (LHSV) varies at a rate between about 0.01 and 10 hours$^{-1}$ and most preferably from about 0.5 to about 4.0 hours$^{-1}$.

The process can be conducted by either continuous, semi-batch or batch methods. The feed streams can be passed through a fixed catalyst bed or into a fluidized reactor in which the catalyst is present in finely divided form. In a preferred method, continuous operation is maintained by feeding the alcohol and aldehydic or ketonic compound into a reactor at the desired temperature and pressure. The reactor is preferably comprised of tubes containing the catalyst, although many other designs are known in the art. After contacting the catalyst the effluent is separated from the catalyst by conventional means, if necessary, and the products recovered. Most commonly distillation is employed to separate the reaction products into the desired components. Unreacted materials are advantageously recycled to the inlet of the reactor.

In particular, the method of the present invention is especially preferred for the conversion of acrolein to allyl alcohol using an alcohol, preferably a secondary alcohol as the hydrogen donor. The reaction using isopropanol as the hydrogen donor is presented below.

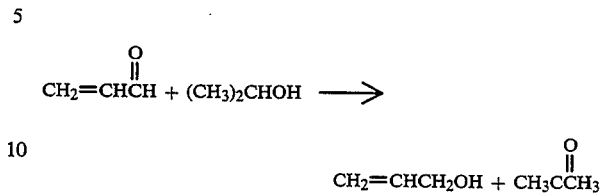

The acrolein to allyl alcohol reaction is conducted at a temperature ranging from about 100° to about 225° C., preferably from 135° to about 220° C. and most preferably from 160° to about 200° C. Reaction pressure may vary widely from 15 to 1000 psia. Preferably the reaction is conducted at a pressure such that the reactants are in the liquid phase. The LHSV of the reactants typically is from about 0.05 to about 12.0 hours$^{-1}$ and preferably from about 0.5 to 4.0 hours$^{-1}$.

The acrolein which is to be converted to allyl alcohol is preferably substantially anhydrous. Substantially anhydrous, as used herein is defined as the removal of water to less than 3.0 weight percent from the acrolein. Commercial grade acrolein typically contains 2-5% by weight water. It is desirable to use substantially anhydrous acrolein because water adversely effects the activity of the catalyst.

Preferably acrolein is also inhibited with free radical scavenger(s) to prevent its undesired free radical polymerization. Free radical scavengers at levels of from about 10 to about 2000 parts per million are advantageously employed, preferably from about 800 to about 1200 and most preferably 1000 parts per million based on the weight of acrolein. Hydroquinone is especially preferred although many other inhibitors known in the art may be employed.

The aforementioned polymer formation can adversely effect catalyst activity. It has been surprisingly discovered that catalytic activity can be regained by heating the catalyst to a temperature exceeding 200° C., preferably exceeding 275° C. in an oxygen containing atmosphere, to regenerate the catalyst to substantially the same catalytic activity as the catalyst originally possessed. More preferably the catalyst is regenerated by heating the catalyst to a temperature exceeding 300° C. in an oxygen-containing atmosphere. Without wishing to be bound to a particular theory it is believed that polymer from the catalyst oxidizes to carbon dioxide and water in the high temperature thereby regaining surface area lost by polymer buildup on the catalyst.

Whereas the exact scope of the present invention is set forth in the appended claims, the following specific examples illustrate certain aspects of the present invention and, more particularly point out methods of evaluating the same. However, the examples are set forth for illustration only and are not to be construed as limitations on the present invention except as set forth in the appended claims. All parts and percentages are by weight unless otherwise specified.

DESCRIPTION OF THE REACTOR

A vertical 316 stainless steel pipe reactor with an outside diameter of 1.91 centimeters and an inside diameter of 1.4 centimeters was used in the following Examples. The reactor was 91 centimeters in length. A 3 millimeter outside diameter thermocouple well was centered in the reactor with ten thermocouples spaced 3.8 centimeters apart. The catalyst bed was located between thermocouple 4 and 9 (thermocouple 1 was located on top). The liquid reactants were fed through the bottom using a plunger pump. The bottom 33 centimeters of the reactor was the preheat zone. The feed then enters approximately a 9 centimeter bed of ⅛-inch glass balls, followed by approximately 20 centimeters of the particulate catalyst, having an approximate volume of 30 cubic centimeters, and an approximate mass of 14 grams. The catalyst bed was topped with 26 centimeters of ⅛-inch glass balls.

The reactor was equipped with four electric heaters (600 watts), each independently controlled on the outside of the 1.91 centimeter outside diameter purge.

A pressure sensor and controller activates a pneumatic valve which was on the cold side of a small heat exchanger.

Analytical samples (1–2 milliliter) were removed from the product stream and analyzed.

ANALYTICAL PROCEDURE

The samples were analyzed using a Hewlett Packard 5890-A gas chromatograph (flame ionizing detector, helium carrier gas at 40 pounds per square inch) and a 30 meter capillary column coated with Supelco Wax-10 ® (Carbowax ®). The sample to be analyzed (approximately 0.05 microliter) was injected into the 300° C. injection port with the column held at 40° C. for 5 minutes. The sample temperature is then ramped at 10° C. per minute until reaching 200° C. The column was then held at 200° C. for approximately 10 minutes.

CATALYST PREPARATION

A bead-type silica with a particle size of 5–10 mesh known as Cariact-10 (available from Davison Chemical Division, W.R. Grace & Co.) was used as the support. The silica was an amorphous silica with a surface area of 300 square meters/gram and a pore volume of 1.02 cubic centimeter/gram. The silica had a uniform pore diameter of approximately 100 Angstroms.

Twenty-five grams of the silica beads were contacted with a solution of 2.54 grams of $ZrO(NO_3)_2$ (equivalent to 1 gram Zr, obtained from Alfa Chemical Co.) dissolved in approximately 40 milliliters of distilled water. The solution was completely imbibed by the catalyst beads. The silica and zicronium-containing solution were well mixed until all the beads were clear.

The beads were then allowed to dry (approximately 18 hours) in air at ambient temperature. Dry beads have a slightly hazy appearance. The beads were then heated in air in a 300° C. muffle furnace for three hours. The heated beads weighed 26.3 grams and contained approximately 4 percent by weight $ZrO_2$.

Surface science study of the approximately 4 weight percent $ZrO_2$ on $SiO_2$ was conducted using powder X-ray diffraction (PXRD), secondary ion mass spectroscopy (SIMS), scanning electron microscopy (SEM) and X-ray photoelectron spectroscopy (XPS). The XPS in particular, showed that the $ZrO_2$ particles on the $SiO_2$ support were substantially all in the tetragonal crystal form and not in the monoclinic form.

OPERATION OF THE REACTOR

At atmospheric pressure and ambient temperature the reactor was pressured with anhydrous alcohol. The reactor was then brought to temperature and switched to the acrolein feed. After about two hours, steady state conditions were achieved and the product composition was constant. The feed was pumped into the reactor at a rate of 50–150 milliliters/hour which is a liquid hour space velocity of approximately 1.6 to 5.0 for the 30 cubic centimeter catalyst bed volume.

The gross liquid product was cooled by use of a water-cooled heat exchanger and discharged into a 5 percent by weight aqueous $Na_2CO_3$ solution (to neutralize any unreacted acrolein). One milliliter samples of the unquenched product was put into serum stoppered bottles and analyzed by the gas chromotography methods discussed above.

EXAMPLE 1

Various sources of $Zr^{+4}$ on silica support were evaluated as catalysts for the conversion of acrolein to allyl alcohol. The supplier of the zirconium salts and its form is reported below. The method of preparation is also provided. The silica employed was Fuji-Davison Cariact-10, 5–10 mesh beads (W.R. Grace & Co.). After the zirconium source was applied to the silica, the beads were dried at 300° C. in air to convert the zironium to its oxide.

After the catalysts were prepared their effectiveness was evaluated using a 7.2 weight percent acrolein 92.8% isopropanol feed, with a LHSV of approximately 3 at 175° C. and 500 psia.

The results are presented below.

| $Zr^{+4}$ Supplier | J-M[b] | J-M[b] | Aldrich[c] | Aldrich[c] | Aldrich[c] | Aldrich[c] | J-M[b] 20% | Aldrich[d] |
|---|---|---|---|---|---|---|---|---|
| $Zr^{+4}$ Source | $ZrO(NO_3)_2$[a] | $ZrO(NO_3)_2$[a] | $ZrO(NO_3)_2$[a] | $ZrCl_4$ | $Zr(Oipr)_4$ | $Zr(OEt)_4$ Ethanol | $ZrO_2$(Sol) | $ZrO(NO_3)_2$ |
| Method | | Aqueous Soln. to Incipient Wetness Dried in Air | | | Iospropanol Soln. to Incipient Wetness Dried in Air | Soln. +3% Acetic Acid, washed with Hexane, Dried in Air | Dilute Sol with $H_2O$ Air Dried | Aqueous Soln. to Incipient Wetness Air Dried |
| Catalytic Activity | | | | | | | | |
| Acrolein Conv. (%) | 99 | 99 | 99 | 99 | 97 | 96 | 99 | 98[d] 94[d] 96[d] |
| Efficiency to Allyl[e] Alcohol (%) | 90 | 90 | 95 | 90 | 84 | 89 | 88 | 87 90 85 |

[a]Different batches of $ZrO(NO_3)_2$
[b]J-M is Johnson Matthey Company Inc.
[c]Aldrich is Aldrich Chemical Company, Inc.
[d]Triplicate preparation and evaluation
[e]Efficiency to Allyl Alcohol is defined herein as the mole percent acrolein converted to allyl alcohol.

The above results demonstrate the efficiency of the $ZrO_2$ silica supported catalyst in the reaction of acrolein to allyl alcohol prepared by various methods and four different sources of $Zr^{+4}$ sources.

EXAMPLE 2

| Effect of ZrO₂ Concentration on Support On Catalyst Activity | | | | | | |
|---|---|---|---|---|---|---|
| | A | B | C | D | E | F[1] |
| Weight % ZrO₂ | 0.0 | 0.5 | 5.4 | 11.8 | 100 | 5.4 |
| Acrolein Conversion | 8 | 97 | 98 | 99 | 43 | 99 |
| Efficiency to Alkyl Alcohol | 0.0 | 90 | 87 | 88 | 47 | 88 |
| ESCA Results[2] | | | | | | |
| Zr on outside Surface of Pellet (mole %) | 0.0 | 0.6 | 1.9 | 5.8 | 100 | 22.6 |
| Zr on inside Surface of Pellet | 0.0 | 0.1 | 1.4 | 0.9 | 100 | 1.4 |

[1]Dispersion of ZrO₂ solution in water (0.01 micron size ZrO₂ dispersion)
[2]ESCA - electron scattering for chemical analysis The above Example demonstrates several results. The neat or 100% ZrO₂ catalyst (Example E) was not as effective as the ZrO₂ on SiO₂ support catalysts (Examples B, C, and D) as the acrolein conversion and allyl alcohol efficiency indicate.

Example A demonstrates that the SiO₂ support is not active.

Examples B, C, and D demonstrate that the ZrO₂ concentration on the support was not critical.

Finally Example F demonstrates that uniform distribution of the ZrO₂ on or within the support particle is not needed.

EXAMPLE 3

A long-term study of the conversion of acrolein to allyl alcohol was conducted using approximately 4% ZrO₂ (from zirconium oxynitrate) on SiO₂ (Fuji-Davison Cariact-10). A LHSV of approximately 3, using a 12:1 molar isopropanol acrolein feed ration to the reactor at 500 psi was employed.

After 215 hours on stream the catalyst was treated with oxygen containing gas at atmospheric pressure, at a temperature of approximately 300° C. for approximately four or five hours. The following results were obtained.

| Time (hours on stream) | 5 | 158 | 160 | 215 | 238 | 283 | 287 |
|---|---|---|---|---|---|---|---|
| Temperature (°C.) | 175 | 175 | 200 | 175 | 175 | 175 | 200 |
| Acrolein Conversion (weight %) | 98.4 | 90.3 | 94.6 | 85.2 | 86.7 | 88.3 | 96.0 |
| Efficiency to Allyl Alcohol (mole %) | 77.1 | 79.8 | 77.3 | 79.5 | 61.9 | 68.9 | 73.3 |
| Product Analysis (gas chromatography area percent) | | | | | | | |
| Acrolein | 0.11 | 0.70 | 0.39 | 1.07 | 0.96 | 0.84 | 0.29 |
| Acetone | 6.25 | 5.82 | 6.15 | 5.57 | 5.28 | 5.41 | 6.25 |
| Allyl Alcohol | 5.66 | 5.37 | 5.67 | 5.05 | 4.00 | 4.54 | 5.25 |

The above results demonstrate that the ZrO₂/SiO₂ catalyst can be regenerated by heating the catalyst in an oxygen-containing atmosphere. Furthermore, when the reaction temperature was raised from 175° C. to 200° C. the acrolein level decreased (0.39 and 0.29) versus the acrolein level at 175° C. (0.70, 1.07, 0.96 and 0.84).

EXAMPLE 4

The catalytic activity of various metal oxides on silica support was evaluated by converting acrolein to allyl alcohol. Aqueous metal nitrate solutions were used to impregnate Cariact-10, 5–10 mesh silica to incipient wetness. The silica was then air dried and them oven heated at 300° C. or 425° C. for 3 hours in air. The catalyst was then placed in the reactor and a 7.1% acrolein in isopropanol feed, having a LHSV of approximately 3.3 was feed through the catalyst at 175° C. and 500 psi. The acrolein conversion and allyl alcohol efficiency are presented below for the various catalysts.

| Metal Oxide/ on SiO₂ | TiO₂ | ZrO₂ | HfO₂ | V₂O₅ | Nb₂O₅ | Ta₂O₅ | Al₂O₃[1] | In₂O₃ | ZnO | Sc₂O₃ | Y₂O₃[1] | La₂O₃[1] | Nd₂O₃[1] | Gd₂O₃[1] | CeO₂ |
|---|---|---|---|---|---|---|---|---|---|---|---|---|---|---|---|
| Acrolein Conversion (weight %) | 55 | 98 | 100 | 34 | 72 | 98 | ~54 | 20 | 49 | 70 | 47 | 27 | ~64 | ~59 | 19 |
| Efficiency to Allyl Alcohol (mole %) | 55 | 87 | 88 | 58 | 56 | 80 | 0 | 0 | 19 | 35 | 19 | 0 | ~18 | ~15 | 29 |

[1]Dried at 425° C. in air for 3 hours

The above results demonstrate the efficiency of the ZrO₂, HfO₂, Ta₂O₅ TiO₂, NbO₅ and V₂O₅ catalysts in converting acrolein to allyl alcohol.

EXAMPLE 5

A ZrO₂ was prepared by mixing Degussa zirconium dioxide (Degussa Corp., Pigment Division, having a surface area of approximately 40 square meters/gram, 300 Angstrom average particle size with greater than 97% of the ZrO₂ having a monoclinic crystal form) with Ludox 40 (Dupont a colloidal SiO₂—NH₄+ counterion) dried in air and heated to 450° C. for 20 minutes. The resulting catalyst had a surface area of 40 square meters/gram and approximately 300 Angstrom particle size. The resulting catalyst was found to contain approximately 44% ZrO₂ and 56% SiO₂.

The catalyst was then placed into service in the reactor using the conditions described in Example 4. The acrolein conversion was 23% and the efficiency to allyl alcohol was 36%. The diminished catalytic activity is believed to be caused by the low surface area of the fumed silica support and the ZrO₂ being predominately in the monoclinic crystalline form.

EXAMPLE 6

In order to evaluate the effect the silica support had an efficiency of the catalyst, two similar silica products were evaluated. One silica was obtained from Fuji-Davison Division of W.R. Grace & Co. (Cariact-10) and the second silica from Philadelphia Quartz (PQ).

The silicas were than used as supports for the $ZrO_2$ catalyst using similar preparation methods. The catalyst were then evaluated by placing the catalysts into service at 175° C., at 500 psia, LHSV of approximately 3, using a 12:1 isopropanol: acrolein molar feed ratio and evaluating the efficiency to allyl alcohol. The following results were obtained.

|  | Cariact-10 | PQ |
|---|---|---|
| size | 5–10 mesh | 1/16 inch extrudate |
| surface area (square meter/gram) | approximately 200 | approximately 210 |
| Pore size (Angstroms) | approximately 100 | approximately 110 |
| Acrolein Conversion (weight percent) | 99 | 96 |
| Efficiency to Allyl Alcohol (mole %) | 90 | 88 |

The above results demonstrate the efficiency of various silica support sources in the present invention.

COMPARATIVE EXAMPLE

A "hydrous" $ZrO_2$ catalyst was prepared using the following procedure. $ZrO_2$ was precipitated using sodium hydroxide from an aqueous $ZrOCl_2.8H_2O$ solution. The precipitate was washed, dried, and heated at 400° C. for 18 hours. This 100% unsupported hydrous $ZrO_2$ catalyst was then evaluated using reaction condition described in Example 6.

The hydrous $ZrO_2$ catalyst yielded an acrolein conversion of 36 weight percent and an efficiency to allyl alcohol of 17 mole percent.

The above results demonstrate that the hydrous $ZrO_2$ material disclosed in the prior art is an inferior catalyst to the predominately tetragonal $ZrO_2$ and metal oxide supported catalysts of the present invention.

EXAMPLE 7

An alumina oxide obtained from United Catalysts Inc., was employed as a support for the $ZrO_2$ catalyst using preparation and reaction conditions specified in Example 6. The ⅛" extrudate was a neutral gamma-alumina oxide derived from a neutral alkoxide.

The $ZrO_2$ on $Al_2)_3$ catalyst produced an acrolein conversion of 59 weight percent an allyl alcohol efficiency of 57 mole percent.

EXAMPLE 8

A 94% sec-butanol/5.9% acrolein stream containing 0.12% hydroquinone was fed to the reactor at 175° C., and 500 psia., with a LHSV of approximately 3. An approximately 4% weight $ZrO_2/SiO_2$ supported catalyst was employed.

The conversion of acrolein to allyl alcohol using sec-butanol was similar to the conversion which resulted when isopropanol was employed as the hydrogen donor.

EXAMPLE 9

An approximately 4 weight percent $ZrO_2$/supported $SiO_2$ catalyst was evaluated in the reduction of acetyl norbornene to 2-(sec-hydroxyethyl)-5-norbornene. Isopropanol was employed as the hydrogen donor at 12:1 alcohol-ketone ratio, with a LHSV of approximately 3 at a temperature from 100°–225° C.

The catalyst provided an 80% conversion of the ketone to the alcohol.

What is claimed is:

1. In a process for converting an $\alpha,\beta$-olefinically unsaturated aldehydic or ketonic compound into the corresponding allylic alcohol derivative which comprises reacting the $\alpha,\beta$-olefinically unsaturated aldehydic or ketonic compound with an alcohol in the presence of a metal oxide catalyst supported on a support; the improvement wherein;

(a) the catalyst is $ZrO_2$
   (b) the support is silica; and
   (c) the reaction is conducted in a liquid phase.

2. The process of claim 1 wherein the $\alpha,\beta$-olefinically unsaturated aldehydic compound is acrolein and the acrolein is reacted with a secondary alcohol to form allyl alcohol.

3. The process of claim 2 which is performed under substantially anhydrous conditions.

4. The process of claim 2 wherein a free radical inhibitor is employed in an amount ranging from 10 about to about 2000 parts per million based on the weight of acrolein.

5. The process of claim 1 wherein the used catalyst is reactivated by an oxygen-containing gas at a temperature in excess of 200° C.

* * * * *